US008918921B2

(12) United States Patent
Mehta

(10) Patent No.: US 8,918,921 B2
(45) Date of Patent: *Dec. 30, 2014

(54) FLUSHABLE URINARY DEVICE AND METHOD FOR DIRECTING URINE INTO A COMMODE FROM A STANDING USER

(76) Inventor: Mahendra Nagindas Mehta, Fort Worth, TX (US)

(*) Notice: Subject to any disclaimer, the term of this patent is extended or adjusted under 35 U.S.C. 154(b) by 153 days.

This patent is subject to a terminal disclaimer.

(21) Appl. No.: 13/368,208

(22) Filed: Feb. 7, 2012

(65) Prior Publication Data

US 2013/0036543 A1 Feb. 14, 2013

Related U.S. Application Data

(63) Continuation of application No. 12/544,913, filed on Aug. 20, 2009, now Pat. No. 8,166,579.

(60) Provisional application No. 61/209,059, filed on Mar. 3, 2009, provisional application No. 61/716,668, filed on May 8, 2009, provisional application No. 61/182,040, filed on May 28, 2009.

(51) Int. Cl.
*A47K 11/00* (2006.01)
*E03D 11/02* (2006.01)

(52) U.S. Cl.
CPC .................................. *E03D 11/025* (2013.01)
USPC ................................................ 4/144.2; 4/342

(58) Field of Classification Search
CPC ....... A47K 11/12; A47K 11/06; A47K 13/08; A47K 17/003; E03D 1/003
USPC .................................................. 4/144.2, 300.3
See application file for complete search history.

(56) References Cited

U.S. PATENT DOCUMENTS 4,985,940 A * 1/1991 Jones ................................ 4/301
6,202,225 B1 * 3/2001 Beck et al. ..................... 4/144.2

* cited by examiner

*Primary Examiner* — Huyen Le
*Assistant Examiner* — Janie Christiansen

(57) ABSTRACT

Flushable urinary device for directing urine into a commode from a standing user comprises an inverted flushable funnel. The inverted funnel ensures picking up the funnel singularly from a nested stack of the funnels. A standing user directs urine into the funnel by keeping upper end of the funnel at urethra and lower end of the funnel relative to the commode to direct urine from the user to the commode. At least one bendable tail portion extends outwardly from the upper end of the funnel and forms a handle for the user to hold the funnel when directing urine into the commode. The funnel is made of flushable bio-degradable material configured to retain a strength and shape temporarily when wetted. It is biodegradable in sewer system. The funnel prevents urine-splatter outside the commode and provides a toilet flushable hygienic means for directing urine into a commode from a standing user.

17 Claims, 8 Drawing Sheets

FLUSHABLE URINARY DEVICE AND METHOD FOR DIRECTING URINE INTO A COMMODE FROM A STANDING USER

CROSS-REFERENCE TO RELATED APPLICATIONS

This application is a continuation of application Ser. No. 12/544,913 filed 2009 Aug. 20, which claims the benefit of U.S. Provisional Patent Application Ser. Nos. 61/209,059, filed 2009 Mar. 3; 61/176,668, filed 2009 May 8; and 61/182,040, filed 2009 May 28.

FEDERALLY SPONSORED RESEARCH

Not applicable

SEQUENCE LISTING

Not applicable

BACKGROUND

1. Field

This application relates to splatter-preventing flushable urinary device and method for directing urine into a commode from a standing user of the commode.

2. Prior Art

The usage of urinals is a known method to urinate in most public restrooms. However, most residences and many commercial places do not offer the convenience of urinals. Therefore, commodes or toilets designed to receive human waste from a sitting position are also used for urination from a standing position. Typically, users stand to urinate for comfort and to avoid germs on commode seats. In the process, however, urine splatters on rim of the commode and floor around the commode or toilet, no matter how careful the users may be. Even traditional urinals do not prevent urine splatters and consequently odor emanates from them. Urine splashing on water of the commode bowl also leads to a sound that may be embarrassing. Urine splatters result in a non-hygienic condition and requires additional cleaning around the commode. Furthermore, urine splatters can stain a rug, if a rug has been placed near the commode. Some users, risking the spread of germs, raise both lids of the commode to an upright position to urinate into the commode. They seldom put them back, which is inconvenience to the next user. From this point ahead in this document, "commodes or toilets" will be referred to as "commodes."

Standard commodes and urinals are two separate fixtures requiring separate spaces, drains, and plumbing lines, which cost a lot more than a single fixture. Several attempts have been made in past to combine a urinal and a commode to provide an economical and space-saving solution. U.S. Pat. No. 6,408,449 issued to Aguirre (2002) disclosed a toilet assembly in combination with a urinal. However, this assembly can be very expensive, because it requires extra floor space and plumbing lines. Most existing toilets do not have the extra space required to add a urinal. In U.S. Pat. No. 5,655,230 issued to Corbin (1997), and in U.S. Pat. Nos. 3,412,408 and 3,500,480 issued to Michal (1968 and 1970 respectively), urinal attachments for toilet bowls are presented. Although these types of urinal attachments can be added to existing toilets, they will make the toilet space more crowded, stinky and unpleasant. These urinal attachments require skilled personnel to install the attachments resulting in extra expenses, time, efforts, and inconveniences. Other prior art devices include U.S. Pat. Nos. 3,822,419; 4,137,579; 4,180,875; and 4,750,219. Most of these prior art devices require significant bathroom modification and plumbing work, which may be unappealing to users.

SUMMARY

A device for directing urine into a toilet aperture from a standing user comprises an inverted, tapered funnel. The funnel comprises a plurality of walls, a first end and a second end. The first end comprises a first opening formed by upper ends of the walls. The second end comprises a second opening formed by lower ends the walls. The first opening is smaller than the second opening, and a passage extends between the first end and the second end. Urine is directed from a standing user into the first opening, flows through the passage and exits the funnel through the second opening and into the toilet aperture. The funnel further comprises at least one bendable tail portion that extends outwardly from the upper end of one of the walls adjacent the first opening. The bendable tail portion forms a handle to be grasped by a user. The funnel is made of a flushable, biodegradable material configured to retain its strength and shape temporarily when wetted. The material is bio-degradable in sewer system. The funnel has transitory surface water repellency to at least one surface without impairing the ability of the funnel to be disposed of by flushing. The funnel is part of a nested stack of funnels. The funnels can comprise a lip that forms a lip extending outwardly and around the second opening. The lip is configured to enable dispensing the funnel singularly from a nested stack of the funnels. The funnel further comprises a second bendable tail portion extending outwardly adjacent the first opening at a wall opposite to the wall on at least one tail portion is located. The second bendable tail portion forms a second handle to be grasped by a user. The bendable tail portion is made of flushable, bio-degradable material configured to retain its strength and shape temporarily when wetted.

A method for directing urine into a toilet aperture from a standing user of the toilet aperture comprises providing a supply of inverted, tapered funnels. Each funnel comprises a plurality of walls, a first end and a second end. The first end comprises a first opening formed by upper ends of the walls. The second end comprises a second opening formed by lower ends of the walls. The first opening is smaller than the second opening, and a passage extends between the first end and the second end. Urine is directed from a standing user into the first opening, flows through the passage and exits the funnel through the second opening and into the toilet aperture. Each funnel further comprises at least one bendable tail portion that extends outwardly from the upper end of one of the walls adjacent the first opening. The bendable tail portion forms a handle to be grasped by a user. The funnel is made of a flushable, bio-degradable material configured to retain its strength and shape temporarily when wetted. The method further comprises removing a funnel from the supply of funnels. Suspend the funnel above the toilet aperture to provide a path for urine from a standing user to the toilet aperture. Direct urine into the suspended funnel to funnel the urine into the toilet aperture. Release the suspended funnel and allow the funnel to drop into the toilet aperture. Flush the toilet aperture to flush away the dropped funnel. The funnel is suspended by a tail portion. The funnel can be suspended by deploying a movable arm. The movable arm can be returned to a stored position after finishing directing urine into the suspended funnel to funnel the urine into the toilet aperture.

A flushable urinal device for directing urine into a commode from a standing user of the commode comprises a funneling-element means. The funneling-element means comprises two ends, each end is open, and a passage extends between the two ends. The funneling-element means can funnel urine from one end to the other end. A biodegradable means admixed with the funneling-element means for biodegrading the funneling-element means in sewage system. The funneling-element means directs urine into a commode from a standing user and prevents urine-splatter outside the commode. The funneling-element means provides a hygienic commode-flushable means for funneling urine into a commode from a standing user of the commode.

ADVANTAGES

The splatter-preventing flushable urinary device for directing urine into a commode from a standing user alleviates deficiencies of prior arts in the same field and provides further benefits including:

(a) Prevents urine-splatters around the commode and keeps bathroom clean.

(b) Makes bathroom cleaning easier, quicker and cheaper.

(c) Conserves water, toxic cleaning chemicals and cleaning labor (d) Requires no additional floor space.

(e) Requires no additional plumbing work.

(f) Installs easily by a layperson in a short time and without any tool.

(g) Has a storage space for extra flushable funnels and toilet paper rolls.

(h) Is hygienic, economical, novel, unique, useful, convenient and pleasing.

DRAWINGS

Brief Description of Drawings

In the drawings, like reference numbers among different embodiments indicate like parts or components. Closely related figures have the same numbers but different alphabetic suffixes.

DRAWINGS

Reference Numerals

| 100 | urinal apparatus | 200 | commode |
| --- | --- | --- | --- |
| 11 | power-driven dispenser | 201 | commode seat |
| 12 | jaw | 203 | commode cover |
| 13 | movable arm | 205 | water tank |
| 14 | end plate | 207 | commode bowl |
| 15 | flushable funnel | 209 | wall |
| 16 | activation device or sensor | 211 | water supply |
| 17 | sleeve | 213 | drain or sewage line |
| 18L | container | 18R | container |
| 20L | fastening device | 20R | fastening device |
| 21 | drawer | 22 | storage section |
| 23 | hub | 24 | height adjusting device |
| 25 | biasing device | 26 | restraining arms |
| 27 | tail portion | 28 | reversible motor |
| 29 | reversible motor | 30 | switch |
| 31 | switch | 32 | core |
| 33 | groove | 34 | track |
| 35 | battery | 36 | electric plug |
| 37 | pivot | 38 | stop |
| 39 | projection | 40 | tongue |
| 41 | channel | 42 | lid |
| 43 | lip | 44 | flange |
| 45 | ball | 46 | socket |
| 47 | additional tail portion | 48 | notch |
| 49 | band | 50 | sear |
| 51 | rack | 52 | pinion |

DETAILED DESCRIPTION OF EMBODIMENTS

Figure 1:
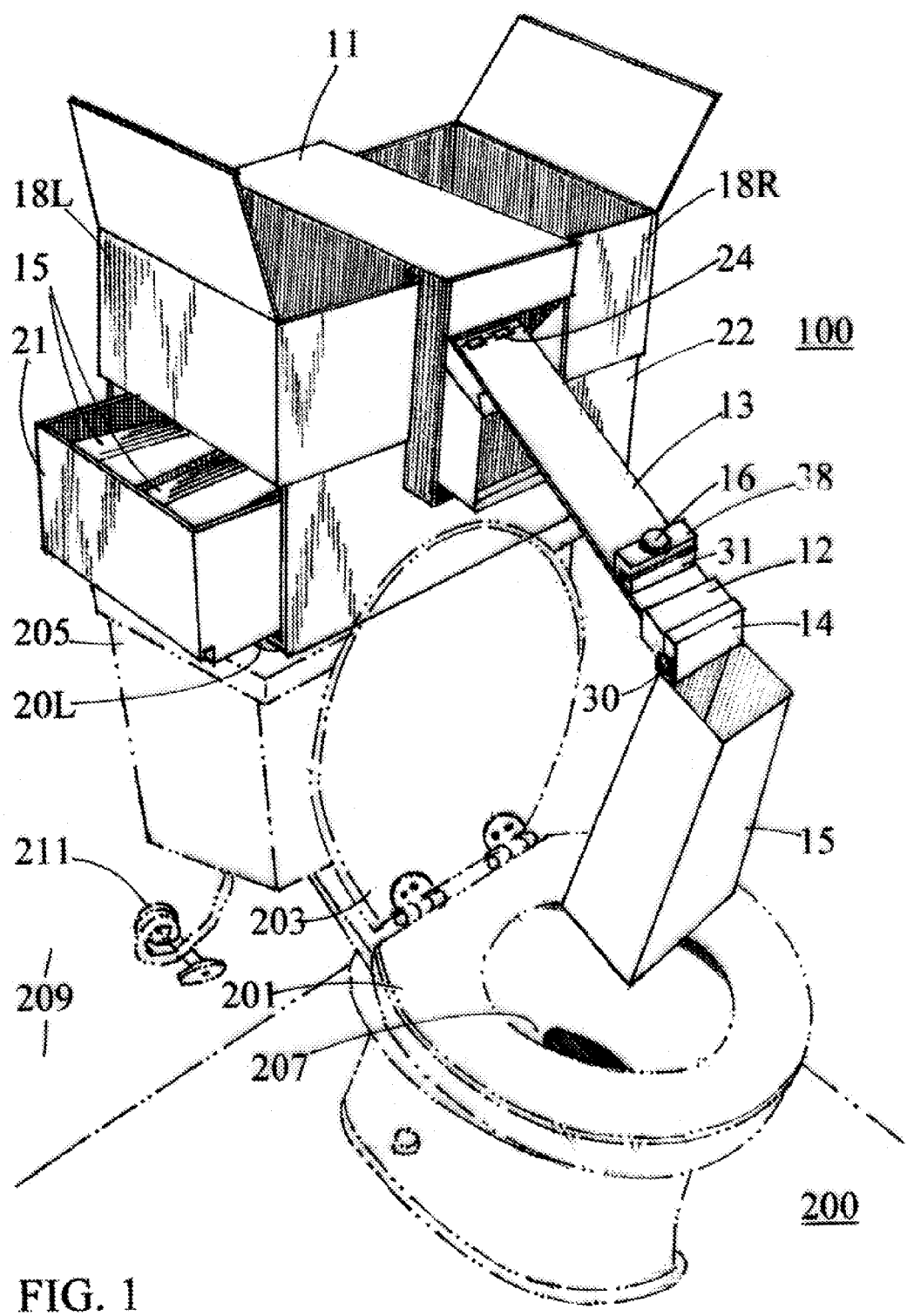
FIG. 1 is a perspective view showing a suspended flushable funnel ready for use to direct urine from a standing user into a commode.

FIG. 1 is a perspective view of the sensor activated apparatus 100 placed on the water tank 205 of the commode 200. The movable arm 13 is extended out (upon first activation by a user) by the power-driven dispenser 11 suspending a funnel 15 over the commode bowl 207. This posture is now ready for use to urinate from a standing position and to prevent urine splatters outside the commode. This is also a temporary conversion of the commode 200 into a splatter-preventing urinal. The jaw 12 is holding a suspended funnel 15 against the end plate 14. The dispenser 11 is placed on the storage section 22. The drawer 21 is shown slightly open to show that it can store extra funnels 15. Containers 18L and 18R are shown open to show that they can store toilet paper rolls. The sensor 16 is placed on the stop 38 but it can be placed anywhere on the apparatus. First activation of the sensor 16 moves the jaw 12 forward clamping the funnel 15 and activates the switch 30. This activation extends the arm 13 forward to suspend the funnel 15 above the commode bowl 207. Second activation of the sensor 16 moves the jaw backward releasing the funnel 15 into the commode bowl 207 and activating the switch 31. This activation returns the arm 13 into the apparatus and keeps the commode unimpeded. The full operation is discussed previously, and in FIG. 3A, FIG. 5, and FIG. 7.

In phantom lines, FIG. 1 illustrates the commode 200, which includes commode seat 201, commode cover 203, water tank 205, and commode bowl 207. The commode may be positioned against a wall 209 and is connected to a water supply 211 and a drain line 213 (see FIG. 3B).

FIG. 1 further shows the sensor activated apparatus 100 includes the fastening devices 20L and 20R (20R not shown in FIG. 1), which attach the apparatus 100 to the water tank 205. Additionally, the storage section 22 can be placed so that the drawer 21 can open from the left side or from right side; it can also be opened from the front or can be designed with a lid on any side. The dispenser 11, the storage section 22 including the drawer 21, the containers 18L and 18R, can be made from rigid or semi-rigid plastic or other suitable materials.

FIG. 1 further shows the movable arm 13 has the height adjusting device 24 such as a constant torque friction hinge. The device 24 allows the user to position the height of the top end of the funnel 15 over the toilet to a suitable height. The device 24 holds the position until second activation of the sensor 16. The second activation moves the arm 13 back into the dispenser 11. Several constant torque friction hinges are available in the market, such as Reell's patented hinge.

Figure 2:
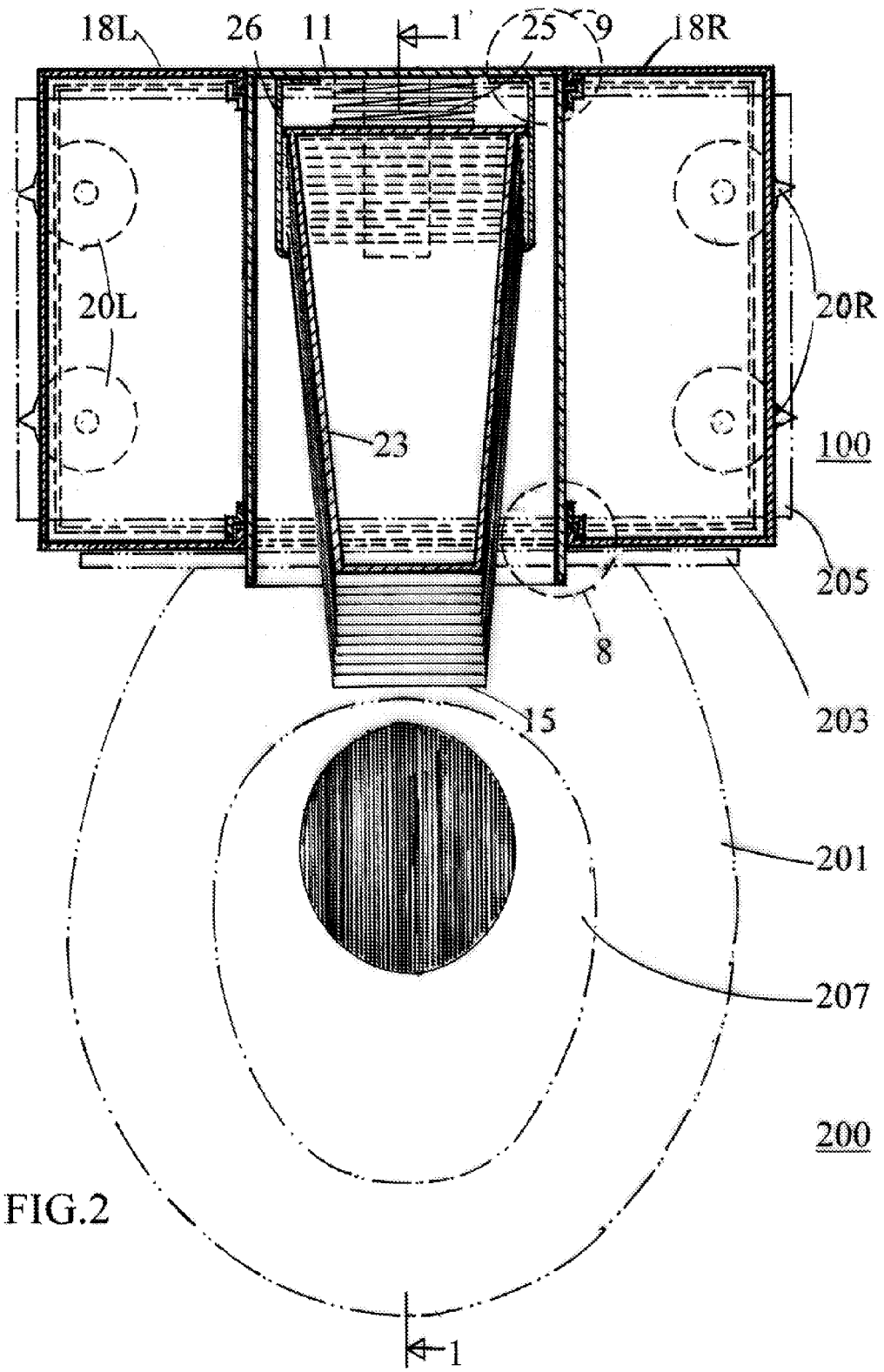
FIG. 2 is a top cross-sectional view of a funnel dispensing apparatus, indicated by the section lines 2-2 in FIG. 3A.
Figure 8:
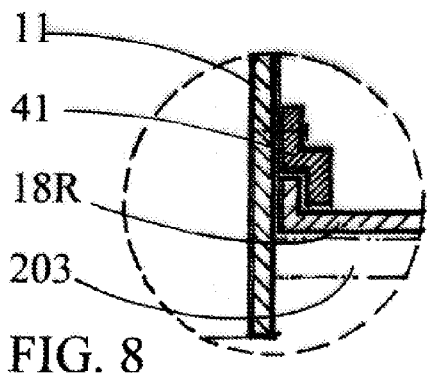
FIG. 8 shows details of the front joint between the container and the dispenser, indicated by the dashed circle 8 in FIG. 2.
Figure 9:
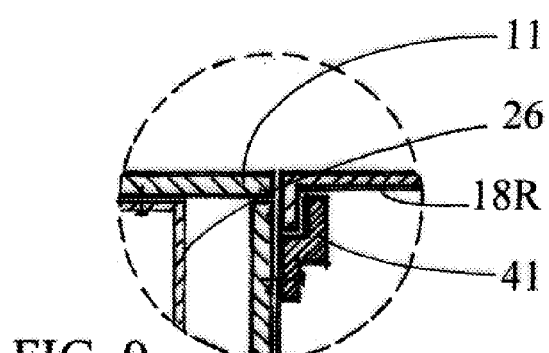
FIG. 9 shows details of the rear joint between the container and the dispenser, indicated by the dashed circle 9 in FIG. 2.

FIG. 2 is a top cross-sectional view of the sensor activated apparatus 100 showing the dispenser 11 including the hub 23. The containers 18L and 18 R can store toilet paper rolls or other items. The restraining arms 26 are anchored to the dispenser 11. A plurality of the funnels 15 in nested stack is placed on the hub 23. The biasing device 25 pushes the hub 23 outwards. The movable arm 13 (not shown in FIG. 2), with cooperation of the restraining arms 26, dispenses a funnels 15 one at a time. The restraining arms 26 can have a portion extended inwards to hold the protrusions 43 (not shown on FIG. 2) of the funnels 15. The arms 26 are flexible enough to release the funnels 15 one at a time. Details at dashed circle 8 and 9 are shown in FIGS. 8 and 9, respectively.

In phantom lines, FIG. 2 shows the commode seat 201 in seating position, the commode cover 203 in upright position, the water tank 205 below the apparatus 100, and the commode bowl 207 of the commode 200.

In dashed lines, FIG. 2 show fastening devices 20L and 20R, which can be made of flexible plastic suction cups or other appropriate fastening device. The fastening devices 20L and 20R are built below the apparatus 100 and are sized to fit on and secure to the water tank 205. The apparatus 100 can be made attachable to the water tank or an object including a wall by way of suitable fastening device.

Figure 3A:
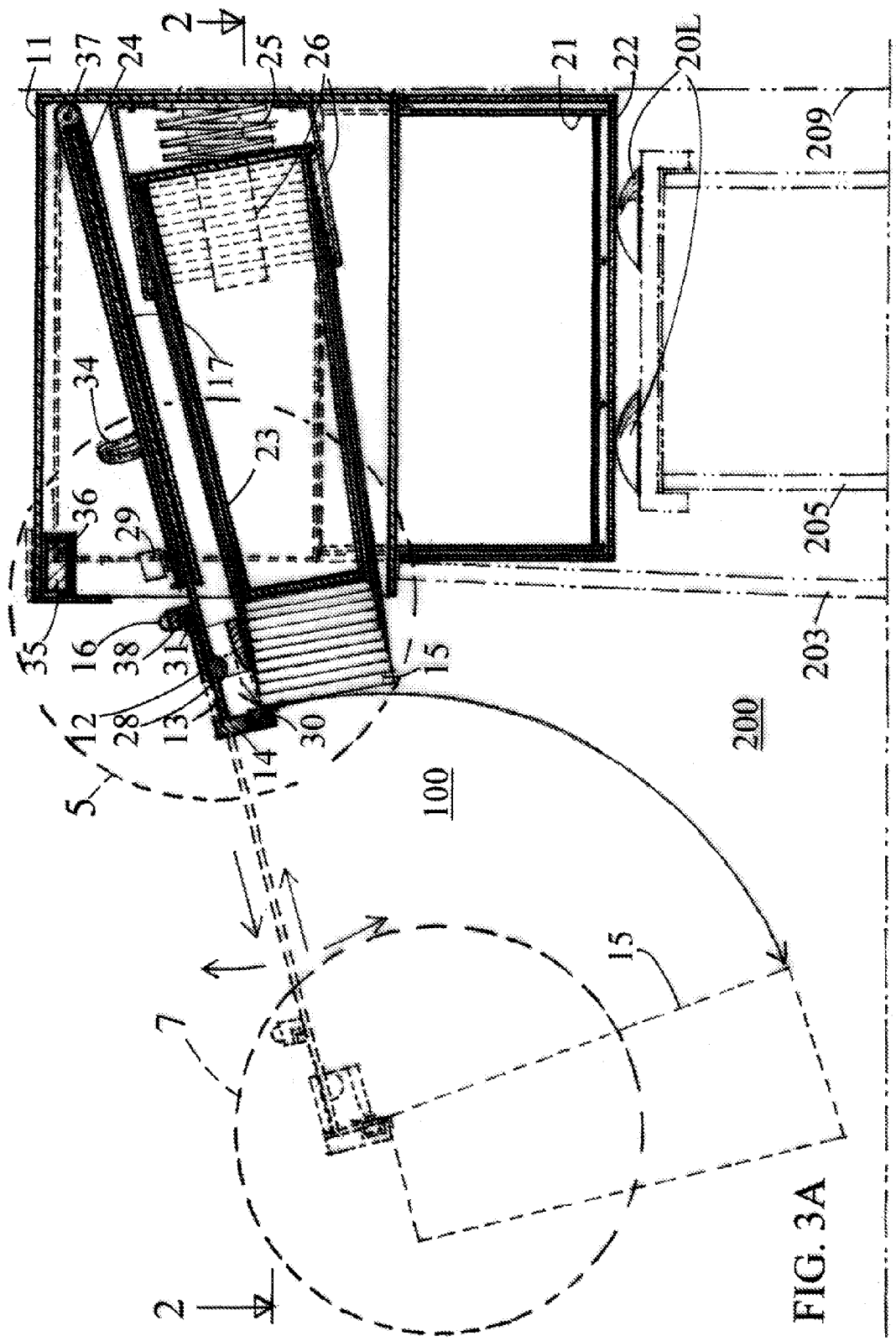
FIGS. 3A and 3B show a side cross-sectional view of the funnel dispensing apparatus, indicated by the section lines 1-1 in FIG. 2, with FIG. 3A showing the apparatus and FIG. 3B showing a commode.
Figure 3B:
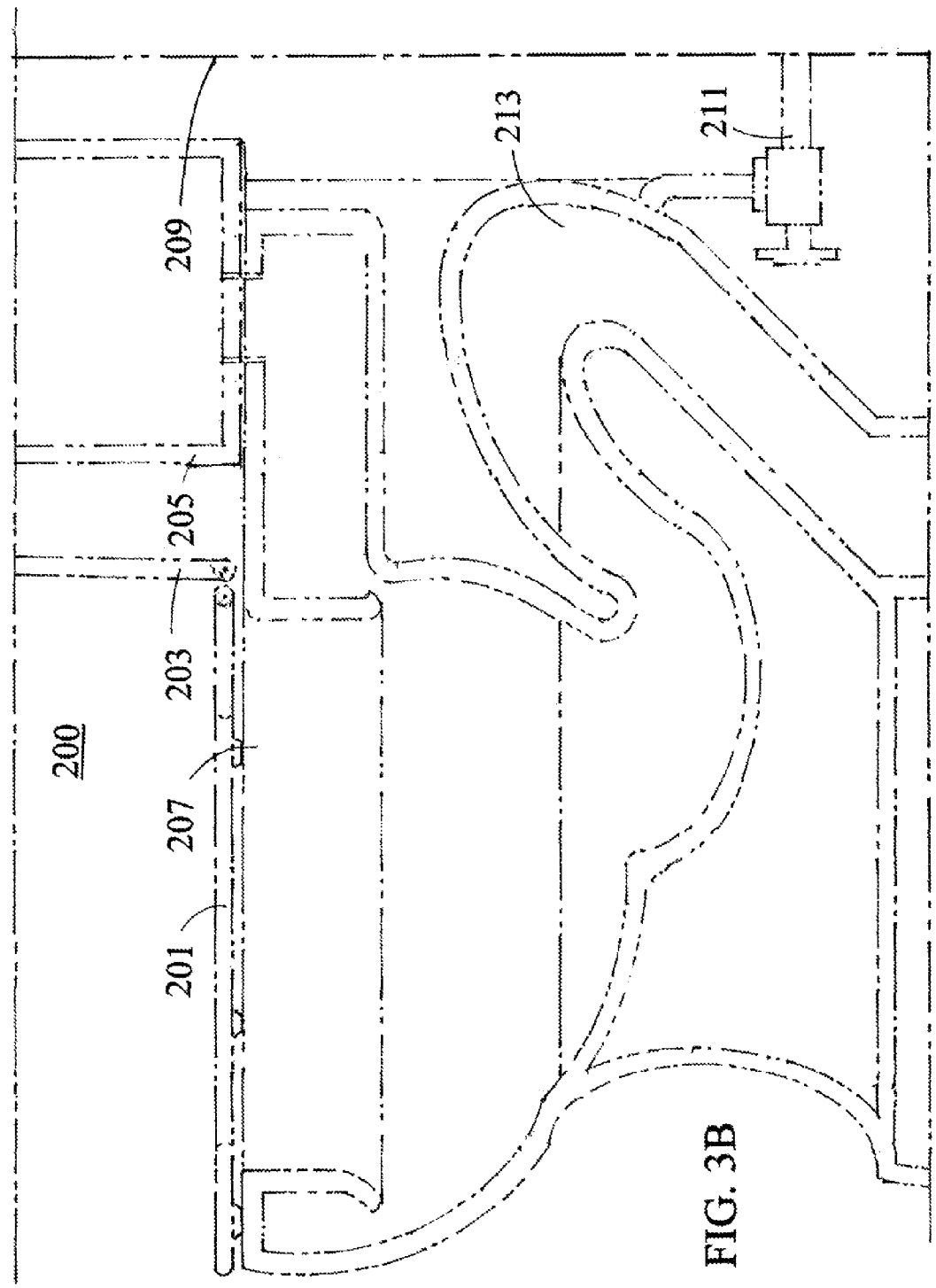

FIG. 3A and FIG. 3B show a side cross-sectional view of the sensor activated apparatus 100 for a commode 200. In solid lines, FIG. 3A shows the apparatus 100 storing a plurality of funnels 15 in nested stack around the hub 23 and a funnel 15 has not been dispensed. The movable arm 13 is in the stored position (shown in solid lines). Upon first activation by a user, the sensor 16 initiates the operation of the motor 28 that moves the jaw 12 forward and clamps the tail portion 27 of the outer most funnel 15 with the end plate 14. Simultaneously, the jaw 12 activates the switch 30, which initiates the operation of the motor 29 to extend the movable arm 13 to the extended position (shown in dashed lines). While extending out, the arm 13 pulls out the clamped funnel 15 from a nested stack on the hub 23. Once the funnel 15 is pulled out completely from the stack (when the larger end of the funnel is pulled out of the stack), the funnel 15 swings from the near horizontal orientation (shown in solid lines in FIG. 3A) to a near vertical orientation (shown in dashed lines in FIG. 3A) due to gravity. The lower end of the funnel 15 positions itself over the bowl 207 so that the urine flows into the bowl 207. The user urinates though the funnel 15. During pull of the funnel 15, the biasing device 25 pushes the hub 23 forward. This positions the next outer most funnel 15 and its tail portion 27 close to the end plate 14, ready to be clamped and dispensed for next user.

Figure 5:
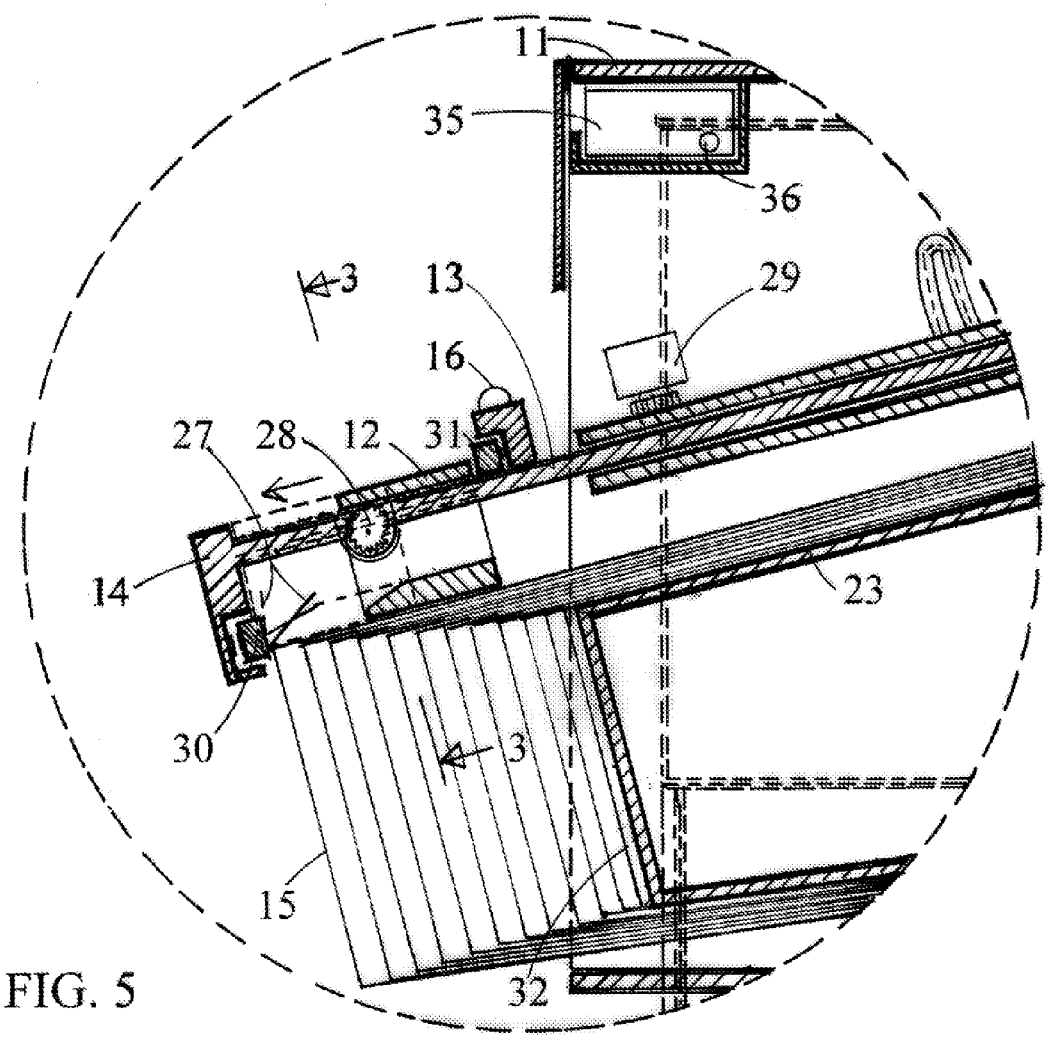
FIG. 5 shows a partial enlarged view of the operation from the stored-hub position, indicated by the dashed circle 5 in FIG. 3A.
Figure 7:
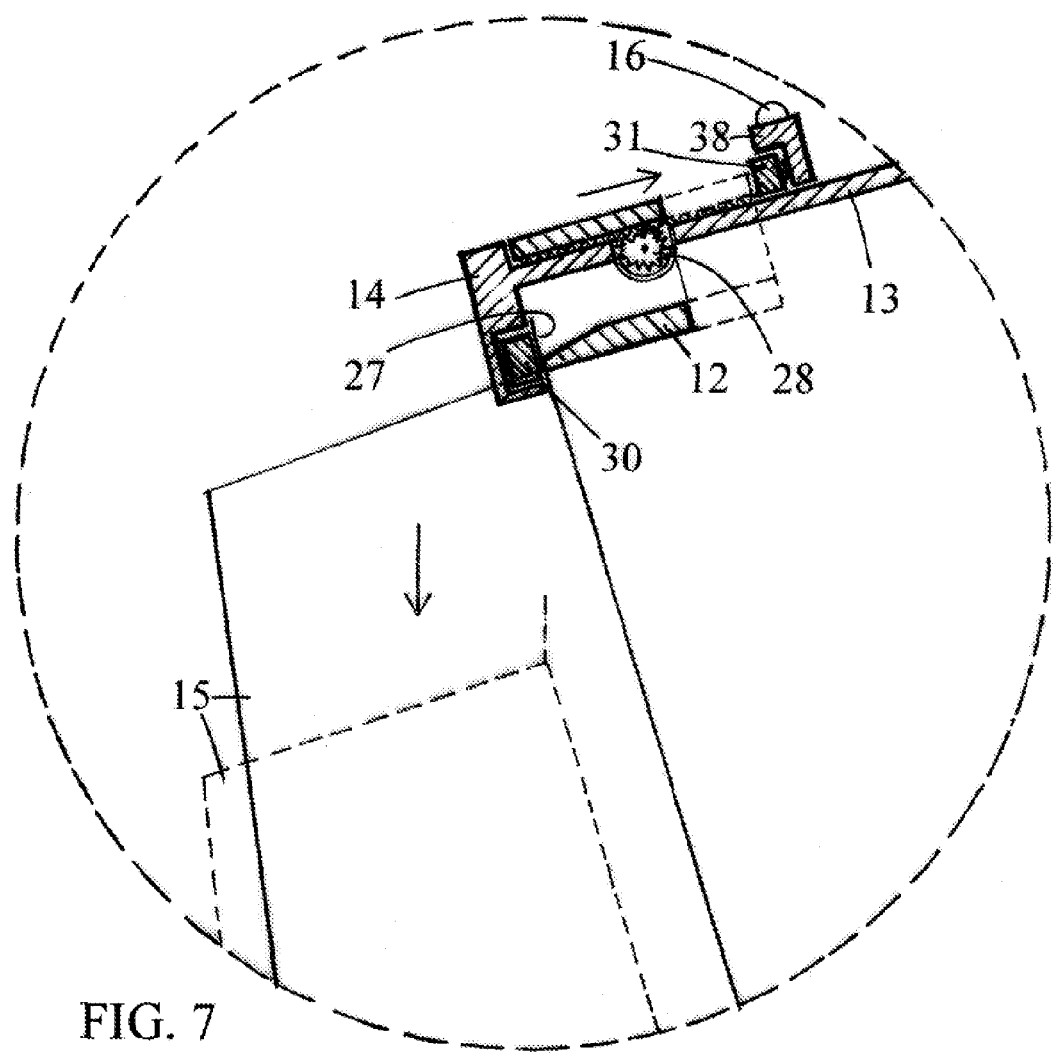
FIG. 7 shows a partial enlarged view of the operation from the dispensed and suspended funnel position, indicated by the dashed circle 7 in FIG. 3A.

When the movable arm is in the extended position (shown in dashed lines), the user activates the sensor 16 after finishing urination. This second activation initiates the operation of the motor 28 that moves the jaw 12 out of the clamping position. This allows the suspended funnel 15 to drop into the commode bowl 207. Immediately following, the jaw 12 activates the switch 31 initiating the operation of the motor 29, which then moves the arm 13 to the stored position. This stored position keeps the commode to function unimpeded. On the next first and second activation, the respective operation repeats. A sleeve 17, which can be a plate, a cylinder or other suitable device, supports the movable arm 13. A pivot 37 and tracks 34 attached on both sides of the dispenser 11 support the sleeve 17. The apparatus 100 is attached by fastening devices 20L, and 20R (not shown in FIG. 3A). The storage section 22 may include a drawer 21 to store extra funnels 15. The movable arm 13 has the height adjusting device 24 for the users to adjust the height of top of the funnel 15 at a suitable height. The motor 28 and 29 can be operated by the battery 35 or the electric plug 36. The details of the operation at dashed circles 5 and 7 are shown in FIGS. 5 and 7, respectively.

In phantom lines, FIG. 3A shows the top part of the commode 200, which can be positioned adjacent to a wall 209. The apparatus 100 can be placed on the water tank 205 (showed in partial view). The water tank is for flushing the commode 200. The commode cover 203, in upright position, appears in partial view.

In phantom lines, FIG. 3B shows the commode 200, which can be used in conjunction with the sensor activated apparatus 100 (shown in FIG. 3A) to convert the commode into a temporary splatter-preventing urinal. The commode 200 includes the commode seat 201, the commode cover 203, the water tank 205, and the commode bowl 207. The commode may be positioned against the wall 209. Water supply 211 supplies water to the water tank 205. The commode is connected to the drain 213.

Figure 4:
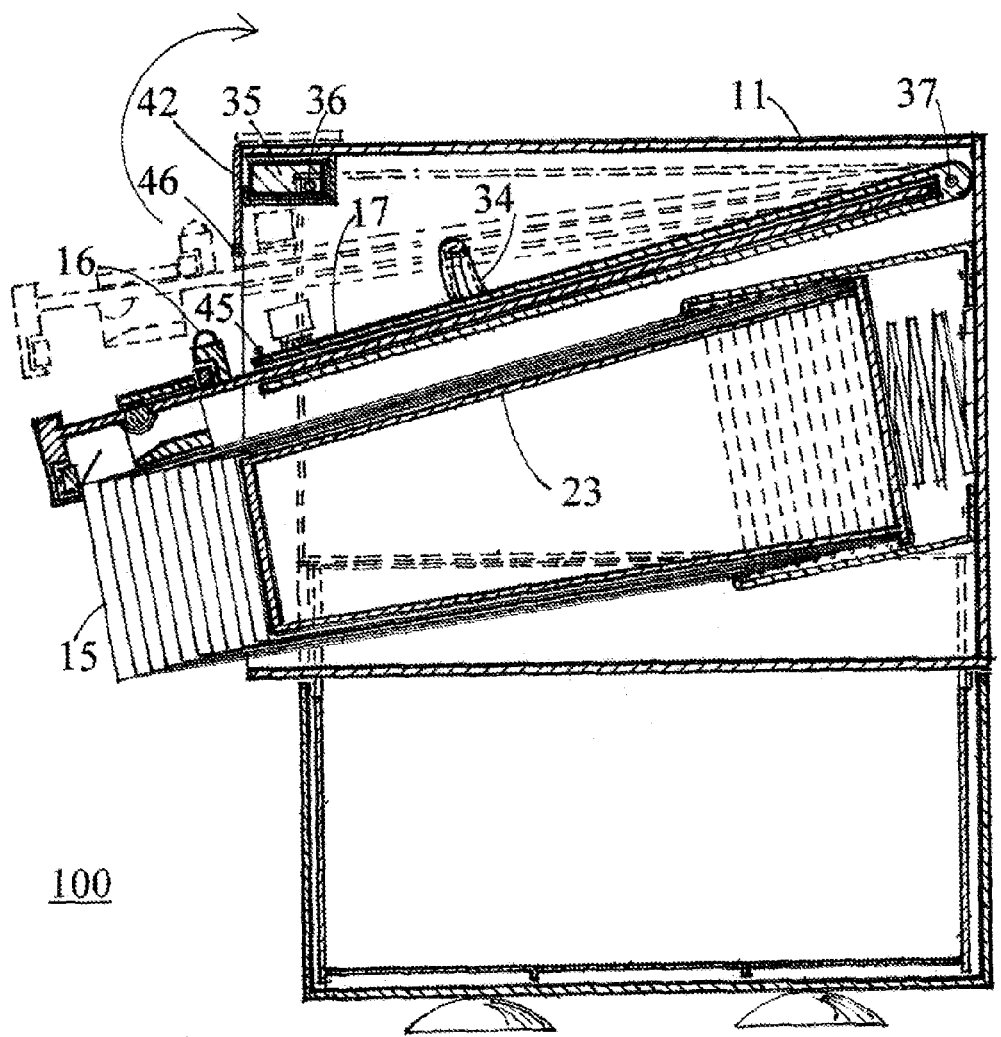
FIG. 4 is an enlarged side cross-sectional view of the funnel dispensing apparatus showing accessibility to the dispenser for restocking the funnels.

FIG. 4 is an enlarged side cross-sectional view of the sensor activated apparatus 100. The sleeve 17 can be moved upward and then reverted back to its original position with aid of the pivot 37 and the tracks 34. A ball 45 mounted on the sleeve 17 snap locks into a socket 46 mounted on a lid 42 to hold the sleeve 17 in upward position, as needed. This feature allows a wider front opening of the dispenser 11 to restock a plurality funnels 15 on the hub 23, as needed. Different methods can be used for this purpose. The hub 23 stores a plurality of funnels 15 in nested stack.

A user activation of the sensor 16 activates the apparatus 100, and in a way converts the commode 200 into a temporary splatter-preventing urinal by suspending a flushable funnel 15 above the commode bowl 207.

FIG. 4 further shows the lid 42 that may be opened to install the battery 35, which can be regular or rechargeable. Several regular or rechargeable batteries are available in the market. Optionally, the electric plug 36 can be used to plug into an electrical wall outlet for direct electric power supply to the apparatus 100.

FIG. 5 shows a partial enlarged view of the apparatus at dashed circle 5 in FIG. 3A. The funnels 15 are stacked in a nested stack around a core 32. The core 32 facilitates insertion of a plurality of the funnels 15 on the hub 23. The reversible motor 28 and the jaw 12 are connected through a rack and pinion device. The motor 28 is attached to the pinion. The jaw 12 is attached to the rack. The reversible motor 29 and the movable arm 13 are connected through a rack and pinion device. The motor 29 is attached to the pinion. The movable arm 13 is attached to the rack.

FIG. 5 further shows that the funnel 15 has not been dispensed. The movable arm 13 is in the stored position. Upon first activation by a user, the sensor 16 initiates the operation of the motor 28. This operation moves the jaw 12 forward, and clamps the tail portion 27 of the outer most funnel 15 with the end plate 14. Simultaneously, the jaw 12 activates the switch 30, which initiates the operation of the motor 29. This process moves the movable arm 13 to the extended position suspending a funnel 15 above the commode. After activating the switch 30 the jaw 12 stops. While extending out, the arm 13 pulls out the clamped outer most funnel 15 from a nested stack of funnels 15 loaded on the hub 23. Near the end plate 14, only one tail portion 27 (of the outer most funnel 15) remains exposed to be clamped. Because of the nested stack, the tail portion 27 of each funnel 15 in the stack is buried below the next funnel 15 stacked above it. Therefore, only one funnel 15 is pulled out at a time, when the user activates the sensor 16. The remaining funnels of the stack remain in place on the hub 23. The restraining arms 26 hold the protrusion 43 of the next funnel 15 in line and in turn hold all remaining funnels 15 to be dispensed (not shown in FIG. 5). In this process, the biasing device 25 (not shown in FIG. 5) pushes the hub 23 forward, which positions the tail portion 27 of the next forward most funnel 15 close to the end plate 14. On the next first activation, the process repeats. The jaw 12 can have a tapered thin leading edge to move under the raised tail portion 27 of the outer most funnel 15. The battery 35 or the electric plug 36 supplies the power.

Figure 6:
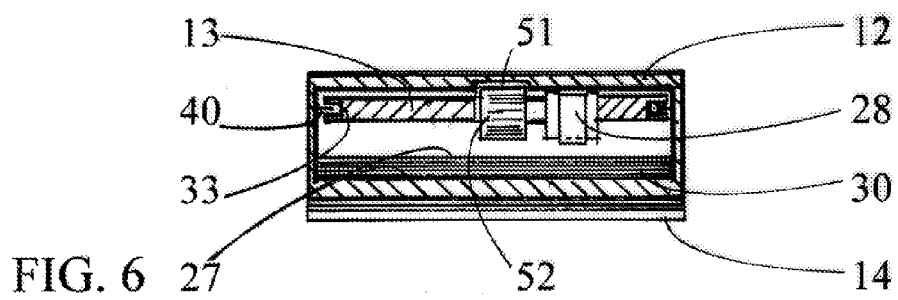
FIG. 6 shows a cross-sectional view of the movable arm, indicated by section lines 3-3 in FIG. 5.

FIG. 6 shows a cross-sectional view of the movable arm 13, indicated by section lines 3-3 in FIG. 5. Upon activation, the jaw 12 slides on the movable arm 13, forward on first activation, and reverse on second activation. A pair of tongues 40 and a pair of grooves 33 keep the reversible jaw 12 aligned and stay on the same plane even while moving. Different methods can be used for this purpose. The tongues 40 are located on both opposite inner sides of the jaw 12. The tongues 40 of the jaw 12 slide in the grooves 33, which are located on both outer sides of the arm 13. The rack 51 of the rack and pinion device is attached to the under surface of the top side of the reversible jaw 12. The pinion 52 is attached to the reversible motor 28. The motor 28 is mounted at the underside of the arm 13 and attaches to the rack 51 through an opening in the arm 13. The tail portion 27, the switch 30, and the end plate 14 are as previously discussed.

FIG. 7 shows a partial enlarged view of the operation from the dispensed and suspended position of the funnel 15, indicated by the dashed circle 7 in FIG. 3A (the dashed lines of FIG. 3A are shown in solid lines in FIG. 7). When the movable arm 13 is in the extended position, the user initiates a second activation of the sensor 16 after urinating. The sensor 16 initiates the operation of the motor 28 to move the jaw 12 out of the clamping position and allows the flushable funnel 15 in the suspended position to drop into the commode bowl 207. Immediately following, the jaw 12 activates the switch 31. The switch 31 initiates the operation of the motor 29, which moves the arm 13 to the stored position. So, the commode 200 remains unimpeded (not shown in FIG. 7). When the arm 13 returns fully in the dispenser 11, the jaw 12 clears the tail portion 27 of the next outer most funnel 15 and allows the tail portion 27 to lift up (not shown in FIG. 7). On next second activation, the process repeats. The activation device or sensor 16 is mounted on stop 38 but can be located anywhere on the apparatus 100 (not shown in FIG. 7). The end plate 14 accommodates the switch 30.

FIG. 8 shows a detail of the front joint, indicated by the dashed circle 8 in FIG. 2. The joint is between the front left corner of the container 18R and the front right side of the dispenser 11 secured by a channel 41. The joint can be nailed, screwed, glued or attached by other suitable method. The commode cover 203 is visible in the FIG. 8.

FIG. 9 shows a detail of the rear joint, indicated by the dashed circle 9 in FIG. 2. The joint is between the rear left corner of the container 18R and the rear right side of the dispenser 11 secured by the channel 41. The joint can be nailed, screwed, glued or attached by other suitable method. The restraining arm 26 is anchored to the dispenser 11.

Figure 10A:
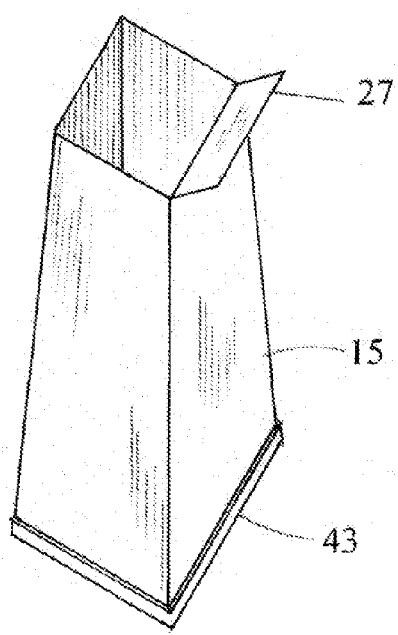
FIG. 10A shows a perspective view of a flushable funnel.

FIG. 10A shows a perspective view of the flushable funnel 15. The funnel 15 is to assist in directing urine into a commode from a standing user of the commode. For directing urine into the commode, the user keeps upper end of the funnel 15 at the user's urethra and lower end of the funnel 15 in middle of the commode. So, the funnel 15 directs the urine into the commode and helps preventing urine-splatter outside the commode. The funnel 15 has a predetermined truncated cone shape, and is made of biodegradable materials. The materials can be compounds or papers having wet strength and water repellency while retaining the property of being flushable. The funnel 15 retains its strength and shape temporarily when wetted. Such papers can be manufactured. For example, U.S. Pat. No. 4,920,171 assigned to Monadnok papers Mills, Inc. (Bennington, N.H.) discloses a paper product suitable for applications requiring wet strength and water repellency while retaining the property of being flushable. The information in U.S. Pat. No. 4,920,171 can be used in its entirety for manufacturing the flushable funnels 15. The U.S. Pat. No. 4,920,171 is directed to a coating composition for application to a flushable cellulosic based waterleaf sheet to impart transitory water repellency to at least one surface of the sheet. Being flushable, the funnel 15 paper have minimum wet strength resin, such as melamine formaldehyde, urea formaldehyde, or a neutral cure wet strength material. Furthermore, the funnel 15 is strong enough to withstand the force of a urine stream. The funnel 15 material can be made moderately slippery so that it can slide out easily from a stack of the funnels 15 stored around core 32 (not shown FIG. 10A). Each funnel 15 has two ends and a passage extending between the two ends. The funnel 15 is tapered so as to have a smaller end and a larger end.

FIG. 10A further shows that the funnel 15 has a bendable tail portion 27 attached on one side of the upper open end. The funnel 15 has a lip 43 all around the larger open end to allow for grip by the restraining arms 26 (not shown in FIG. 10A). The lip extends outwardly and around the lower open end. The lip is configured to enable dispensing the funnel 15 singularly from a nested stack of the funnels 15. The lip 43 cooperates with the restraining arms 26 and the biasing device 25 (not shown in FIG. 10A) to dispense one funnel 15 one at a time from the nested stack of the funnels 15. The funnel 15 can be of different suitable cross-section, shapes and sizes including, but not limited to square, round, oval, rectangular, or polygon. The funnel 15 can be made of suitable lengths to suit different sizes of commodes.

Figure 10B:
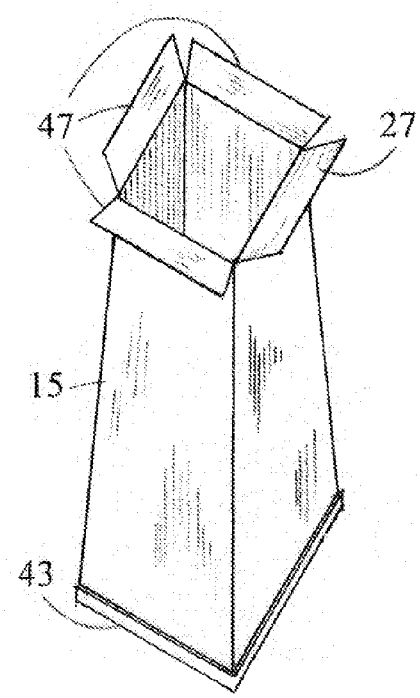
FIG. 10B shows a perspective view of the flushable funnel with additional tail portions.

FIG. 10B shows the funnel 15 with additional tail portions 47 at upper end of the funnel 15. In addition to the entire characteristic described in FIG. 10A including the tail portion 27 and the lip 43, the funnel 15 can have additional tail portion 47 on any or all of the remaining sides of the upper open end. The additional tail portions 47 on two sides can be used as handles or an additional tail portion 47 and the tail portion 27 can be held by both hands of a user during directing urine from a standing position. The additional tail portion 47 on the side close to the user can act as a guard against dripping urine. The funnel 15 can be used with or without the apparatus 100. Without the apparatus 100 (not shown in FIG. 10B), the funnel 15 with the tail portion 27 and additional tail portions 47 (shown in FIG. 10C) can be held in hands by a user over a commode bowl. Then, it can be dropped into the commode bowl after the use, and it can be flushed away.

Figure 10C:
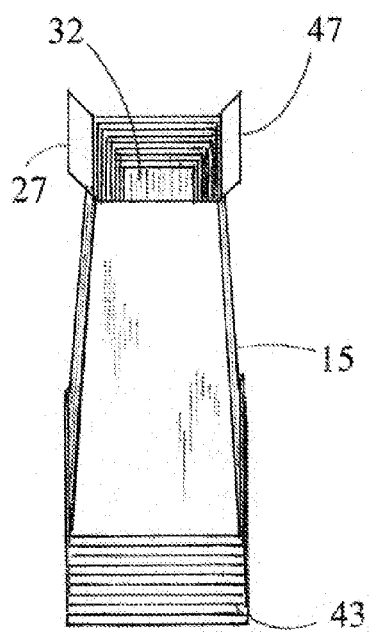
FIG. 10C shows a perspective view of the flushable funnels placed around a cardboard core in a nested stack.

FIG. 10C shows the flushable funnel 15 having an additional tail portion 47 at upper end of another wall of the funnel 15. A plurality of the funnel 15 is arranged in a nested stack around the core 32. In addition to the entire characteristic described in FIG. 10A, including the tail portion 27 forming a handle, the funnel 15 has an additional tail portion 47 on the opposite side of tail portion 27 forming another handle. The two handles can be held by a user to suspend the funnel 15 above the commode bowl for urinating in the commode from a standing position. This method can be used without the use of the apparatus 100 (not shown in the FIG. 10C). After the use, the user drops the funnel 15 in the commode bowl. Then, the user flushes the commode to flush away used funnel 15. The funnel 15 disintegrates in sewers system. The funnels 15 may be with or without the lip 43. This nested stack of the funnel 15 may be stored on top of the water tank of the commode or near the toilet aperture. When needed, a user pulls out one funnel 15 from the stack. Since the lower end is larger than the upper end, the stack of funnels 15 stays stable at the stored position.

Figure 11:
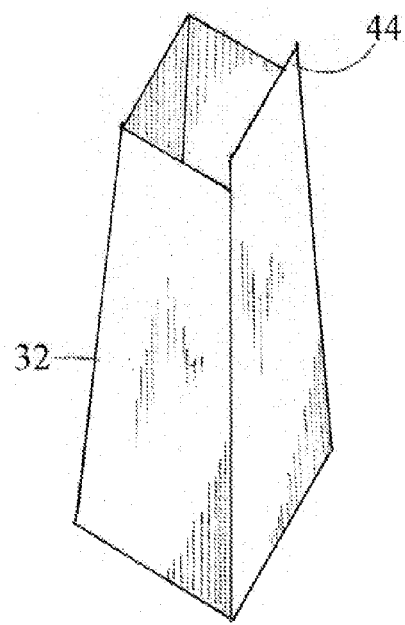
FIG. 11 shows a perspective view of the cardboard core.

FIG. 11 shows a perspective view of the core 32, which can be made from cardboard or another suitable material and thickness. Its function is similar to the cardboard core of toilet paper rolls. The core 32 has a flange 44 for pulling it out from the hub 23 (not shown in FIG. 11). The core 32 can be disposable or refillable.

CONCLUSION, RAMIFICATIONS, AND SCOPE

Thus, the splatter-preventing flushable urinary device for directing urine into a commode from a standing user provides a more reliable, clean, and economical hygienic device that can be used by a wide range of people. The device and the method for directing urine into a commode from a standing user facilitates urinal function without installing a traditional urinal and extra plumbing.

The elements described here can be duplicated or eliminated, changed in size and made in different shapes and colors. They can be connected or associated with adjacent elements in a different manner. They can be made integrally or separately, i.e. modular or in sections.

While my above description contains much specificity, these should not be construed as limitations on the scope, but rather as an exemplification of one embodiment thereof. Accordingly, the scope should be determined not by the embodiments illustrated, but by the appended claims and their legal equivalent.

I claim:

1. A device for directing urine into a toilet from a standing user of the toilet, the toilet having an aperture for receiving human waste, comprising:
    an inverted, tapered funnel body comprising a first wall, second wall, third wall, and fourth wall, a first end and a second end, said first end comprising a first opening formed by upper ends of said first wall, second wall, third wall and fourth wall, and said second end comprising a second opening formed by lower ends of said first wall, second wall, third wall, and fourth wall, wherein said first opening is smaller than said second opening, and a passage between said first end and said second end, wherein urine is directed from a standing user into said first opening, flows through said passage and exits said funnel body through said second opening and into said toilet aperture;
    a protrusion that forms a lip extending outwardly and around said second opening at said lower ends of said first, second, third, and fourth walls, said lip being configured to cooperate with restraining arms of a funnel dispensing apparatus;
    at least one bendable tail extending outwardly from said upper end of said first wall adjacent said first opening, wherein said at least one bendable tail forms a handle for being grasped by a user; and
    at least one fin extending outwardly from said upper end of said second wall adjacent said first opening, said at least one fin configured to act as a guard against dripping urine;
    wherein said funnel body is made of a flushable, bio-degradable material configured to retain its strength and shape temporarily when wetted.

2. The device of claim 1, wherein said funnel is made of material that is bio-degradable in a sewer system, said funnel having transitory surface water repellency to at least one surface of said funnel without impairing the ability of said funnel to the be disposed of by flushing.

3. The device of claim 1, wherein said funnel material further comprising a minimum wet strength resin selected from the group consisting of melamine formaldehyde, urea formaldehyde, and a neutral cure wet strength material.

4. The device of claim 1, wherein said funnel is part of a nested stack of said funnels.

5. A method for directing urine into a toilet from a standing user of the toilet, the toilet having an aperture for receiving human waste, comprising:
    providing a supply of inverted, tapered funnels, each of said funnels comprising a plurality of walls, a first end and a second end, said first end comprising a first opening formed by upper ends of said plurality of walls, and said second end comprising a second opening formed by lower ends of said plurality of walls;
    wherein said first opening is smaller than said second opening, and a passage extending between said first end and said second end;
    wherein urine is directed from a standing user into said first opening, flows through said passage and exits said funnel through said second opening and into said toilet aperture;
    wherein each of said funnel further comprises at least one bendable tail portion extending outwardly from said upper end of one wall of said plurality of walls adjacent said first opening; wherein said at least one bendable tail portion forms a handle for being grasped by a user;
    wherein said funnel is made of a flushable, bio-degradable material configured to retain its strength and shape temporarily when wetted removing a funnel from said supply of funnels;
    suspending the funnel above the toilet aperture to provide a path for urine from a standing user to the toilet aperture;
    directing urine into the suspended funnel to funnel the urine into the toilet aperture;
    releasing the suspended funnel and allowing the funnel to drop into the toilet aperture; and
    flushing the toilet aperture to flush away the dropped funnel.

6. The method of claim 5, wherein the step of suspending the funnel further comprises suspending the funnel by a tail portion.

7. The method claim of 5, wherein the step of suspending the funnel above the toilet aperture comprises deploying a movable arm;

the method further comprising returning the movable arm to a stored position after finishing directing urine into the suspended funnel to channel the urine into the toilet aperture.

8. An apparatus for funneling urine into a toilet from a standing user of the toilet, the toilet having an aperture for receiving human waste, comprising:
   a. a supply of flushable funnels, said flushable funnels being inverted funnels having two ends, one of said ends being smaller than the other, each end being open, and a passage extending between said two ends and said funnel can funnel urine from said smaller end to said other end;
   b. a power-driven dispenser activated by a user, said dispenser being movable under power from a stored position where said dispenser allows unimpeded use of the aperture, and an extended position where said dispenser locates and holds one of said flushable funnels in a suspended position with said smaller end of said flushable funnel above the aperture and said other end of said flushable funnel located relative to the aperture to direct urine from said flushable funnel into the aperture;
   c. said power-driven dispenser further being operable to move said power-driven dispenser under power to cause said dispenser to release said flushable funnel into the aperture and to move said dispenser from said extended position to said stored position.

9. The apparatus of claim 8, wherein the power-driven dispenser further comprises a power-driven movable arm, said movable arm having a means for moving between a stored position and an extended position.

10. The apparatus of claim 8, wherein said dispenser having a means for refilling a plurality of the flushable funnels to the dispenser.

11. The movable arm of claim 9, further comprising a means for releasably clamping a portion of one of the flushable funnels to the movable arm.

12. The movable arm of claim 9, further comprising a sensor for activation by a user of the aperture, said sensor initiating the operation of the movable arm that releasably clamps a portion of one of the flushable funnels to the movable arm and extends the movable arm to the extended position.

13. The movable arm of claim 9, wherein said sensor activation is a first activation, said sensor having a second activation for activation by a user when the movable arm is in the extended position, wherein said second activation of said sensor initiates the operation of the movable arm to release the clamped funnel into the aperture and return the movable arm to the stored position.

14. The apparatus of claim 8, wherein the dispenser includes restraining arms with a portion extending inwards to hold the flushable funnels, and to facilitate releasing the flushable funnels, one at a time.

15. The apparatus of claim 8, wherein the apparatus includes storage space to store extra supplies.

16. The apparatus of claim 8, wherein the apparatus having at least one means for fastening on an exterior of the apparatus for mounting the apparatus to an object.

17. The apparatus of claim 8, wherein the aperture has a water tank, the apparatus is attached to the water tank or attached close to the aperture.

* * * * *

UNITED STATES PATENT AND TRADEMARK OFFICE
CERTIFICATE OF CORRECTION

PATENT NO.       : 8,918,921 B2
APPLICATION NO.  : 13/368208
DATED            : December 30, 2014
INVENTOR(S)      : Mahendra Nagindas Mehta It is certified that error appears in the above-identified patent and that said Letters Patent is hereby corrected as shown below:

IN THE CLAIMS:

Column 10, Claim 5, line 51, please place missing ";" between the words: wetted--;-- removing.

Signed and Sealed this
Thirty-first Day of March, 2015

Michelle K. Lee
*Director of the United States Patent and Trademark Office*